(12) United States Patent
You et al.

(10) Patent No.: US 9,638,684 B2
(45) Date of Patent: May 2, 2017

(54) METHOD OF EVALUATING A CROSSLINKED VINYLPYRIDINE RESIN

(71) Applicant: CHIYODA CORPORATION, Yokohama-shi, Kanagawa (JP)

(72) Inventors: Zhixiong You, Yokohama (JP); Ryuichi Kanai, Yokohama (JP); Yoichi Umehara, Yokohama (JP); Takeshi Minami, Yokohama (JP)

(73) Assignee: CHIYODA CORPORATION, Yokohama-shi (JP)

( * ) Notice: Subject to any disclaimer, the term of this patent is extended or adjusted under 35 U.S.C. 154(b) by 132 days.

(21) Appl. No.: 14/547,989

(22) Filed: Nov. 19, 2014

(65) Prior Publication Data
US 2015/0147816 A1    May 28, 2015

(30) Foreign Application Priority Data

Nov. 22, 2013  (JP) ................................ 2013-241927

(51) Int. Cl.
| G01N 33/44 | (2006.01) |
| G01N 25/12 | (2006.01) |
| G01N 5/04  | (2006.01) |
| G01N 17/00 | (2006.01) |
| B01J 23/46 | (2006.01) |

(52) U.S. Cl.
CPC .......... *G01N 33/442* (2013.01); *B01J 23/464* (2013.01); *G01N 5/04* (2013.01); *G01N 17/00* (2013.01); *G01N 25/12* (2013.01)

(58) Field of Classification Search
CPC .............................. G01N 33/44; G01N 25/12
USPC ..................................... 436/60, 85, 155, 157
See application file for complete search history.

(56) References Cited

U.S. PATENT DOCUMENTS

| 4,663,220 A * | 5/1987 | Wisneski ................. D04H 1/56 |
| | | 428/221 |
| 4,692,371 A * | 9/1987 | Morman ................... D01F 6/42 |
| | | 264/12 |
| 2010/0074083 A1 | 3/2010 | Shibuya et al. |
| 2013/0209768 A1 | 8/2013 | You et al. |

FOREIGN PATENT DOCUMENTS

| JP | 6-315637 A  | 11/1994 |
| JP | 2011-149844 | * 8/2011 |
| JP | 2012-81440 A | 4/2012 |

OTHER PUBLICATIONS

Horrocks, A. R. et al, Journal of Applied Polymer Science 1991, 42, 243-261.*

Kobayashi, K. et al, Proceedings of the 4th international Conference on Properties and Applications of Dielectric Materials 1994, paper 6232 pp. 678-681.*

(Continued)

*Primary Examiner* — Arlen Soderquist
(74) *Attorney, Agent, or Firm* — Westerman, Hattori, Daniels & Adrian, LLP (57) ABSTRACT

Provided is a method of evaluating a resin capable of quantitatively evaluating a deterioration degree of the resin with high accuracy and ease. The method includes evaluating the resin based on a shift of a characteristic peak representing a deterioration degree of the resin, the peak being observed in thermal analysis of the resin by a temperature increase, to lower temperatures.

4 Claims, 8 Drawing Sheets

(56) References Cited

OTHER PUBLICATIONS

Sarma, H. et al, Conference Recod of the 1996 IEEE International Symposium on Electrical Insulation 1996, 624-631.*
Horrocks, A. R. et al, "The Use of Thermal Analysis to Assess Oxidative Damage in Polyolefins" in Oxidative Behavior of Materials by Thermal Analytical Techniques, ASTM STP 1326, Riga, A. T. et al., Eds., American Society for Testing and Materials, 1997, 58-75.*
Jha, A. et al, Polymer Degradation and Stability 1998, 62, 575-586.*
Xie, W. et al, Journal of Applied Polymer Science 2002, 83, 1219-1227.*
Denardin, E. L. G. et al, Thermochimica Acta 2003, 395, 159-167.*
Gupta, Y. N. et al, Journal of Applied Polymer Science 2004, 92, 1737-1748.*
Agic, A. et al, Journal of Applied Polymer Science 2007, 103, 764-772.*
Yin, W. et al, 2008 IEEE International Power Modulators and High-Voltage Conference 2008, 537-542.*
Haas, A, et al, Proceedings of the 16th International Symposium on High Voltage Engineering 2009, paper A-39, 6 pages.*
Chatterjee, A., Journal of AppliedPolymer Science 2009, 114, 1417-1425.*
Weon, J.-I., Polymer Degradation and Stability 2010, 95, 14-20.*
Martinez-Morlanes, M. J. et al, Polymer Testing 2010, 29, 425-432.*
Benabdelghani. et al, Journal of Applied Polymer Science 2011, 121, 462-468.*
Keskkula, H. et al, Journal of Applied Polymer Science 1986, 31, 941-950.*
ten Brinke, G. et al, Colloid & Polymer Science 1989, 267, 992-1001.*
Sartor, G. et al, Journal of Polymer Science: Part B: Polymer Physics 1994, 32, 683-689.*
Li, X.-G., Reactive & Functional Polymers 1999, 42, 53-58.*
Kim, Y. J. et al, Carbohydrate Polymers, 2001, 46, 1-6.*
Kittur, F. S. et al, Carbohydrate Polymers, 2002, 49, 185-193.*
Liu, Y. et al, Journal of Agriculture & Food Chemistry 2006, 54, 5701-5717.*
Saiani, A. et al, Macromolecules 2007, 40, 7252-7262.*
Sato, Y. et a, Journal of Thermal Analysis & Calorimetry 2009, 97, 297-302.*
Gonzalez, D. C. et al, Journal of Food Engineering 2010, 100, 187-193.*
Partial European Search Report dated Mar. 20, 2015, issued in corresponding EP Patent Application No. 14194025.4 (7 pages).
"Measurement of polymer degradation by CL, TGA, DSC, Py-GCMS and SPME-GCMS", Scientific Assessment of Plastics Degradation, Jan. 31, 2012, pp. 177-199, XP055176561, cited in Partial European Search Report dated Mar. 20, 2015 (23 pages).
Nicole E. Zander et al., "Thermal and FTIR Characterization of Poly (4-vinylpyridine) Crosslinked with Metal Salts", Mar. 1, 2010 XP055175569, cited in Partial European Search Report dated Mar. 20, 2015 (18 pages).
A. M. Lyons et al., "Thermal Decomposition of Poly(2-vinylpyridine): Effect of Complexation with Copper Chloride", Journal of Polymer Science Part A: Polymer Chemistry, vol. 28, No. 2, pp. 245-259, Jan. 30, 1990, XP055175566, cited in Partial European Search Report dated Mar. 20, 2015 (15 pages).
Duncan M. Price et al., "Thermogravimetry of Polymers" In: "Encyclopedia of Analytical Chemistry", Jan. 1, 2000, pp. 8094-8105, John Wiley & Sons, Ltd., XP055176505, cited in Partial European Search Report dated Mar. 20, 2015 (13 pages).
Jong J. Lim et al., "Evaluation of Kinetic Parameters of Thermal Decomposition of Native Collagen by Thermogravimetric Analysis", BIOPOLYMERS, Sep. 1, 1974, vol. 13, No. 9, pp. 1791-1807, XP055176557, cited in Partial European Search Report dated Mar. 20, 2015 (18 pages).
Extended European Search Report dated Jun. 12, 2015, issued in corresponding Application No. 14194025.4 (12 pages).

* cited by examiner

METHOD OF EVALUATING A CROSSLINKED VINYLPYRIDINE RESIN

BACKGROUND OF THE INVENTION

Field of the Invention

The present invention relates to a method of evaluating a resin, including evaluating a deterioration degree of the resin.

Description of the Related Art

Acetic acid is a basic chemical that finds use in a wide variety of applications such as raw materials for polyvinyl acetate, acetylcellulose, and acetates, and a solvent for a terephthalic acid-producing plant. A methanol carbonylation method involving carbonylating methanol with carbon monoxide in the presence of a catalyst to produce acetic acid has been known as a method of producing acetic acid.

Available as the methanol carbonylation method is a method involving using, as a catalyst, a solid catalyst obtained by causing a resin as a carrier to carry a precious metal complex on itself such as a catalyst obtained by causing a resin, which has a side chain having a nitrogen-containing aromatic ring group such as a pyridine group and a crosslinking portion, to carry a rhodium complex (see Japanese Patent Application Laid-Open No. H6-315637 and Japanese Patent Application Laid-Open No. 2012-81440).

The methanol carbonylation reaction is performed under heat or pressure (e.g., a condition of a temperature of from 130° C. to 190° C. or a pressure of from 3 to 5 MPa), and hence the resin as a carrier decomposes to deteriorate. As the decomposition progresses, there arises a problem in that the particulate carrier resin is reduced in its average size to clog, for example, a screen to be placed at an outlet of a reactor for the carbonylation reaction, a problem in that the carrier resin is liable to powder owing to a reduction in its crosslinking degree, or a problem in that an amount of the nitrogen-containing aromatic ring group such as a pyridine group on the carrier resin reduces, and hence an ability of the resin to immobilize the precious metal complex made of rhodium or the like reduces, and by extension, an ability of the catalyst reduces.

Therefore, the deteriorated carrier resin needs to be exchanged before any such problem arises. In order that a timing at which the carrier resin is exchanged may be determined, a method of quantitatively evaluating a deterioration degree of the carrier resin with high accuracy and ease has been desired.

It should be noted that such evaluation for the deterioration degree of the resin has been desired not only in the catalyst to be used in the methanol carbonylation reaction but also similarly in any other resin.

SUMMARY OF THE INVENTION

In view of the problems, an object of the present invention is to provide a method of evaluating a resin capable of quantitatively evaluating a deterioration degree of the resin with high accuracy and ease.

According to one embodiment of the present invention for achieving the object, there is provided a method of evaluating a resin, the method including evaluating the resin based on a shift of a characteristic peak representing a deterioration degree of the resin, the peak being observed in thermal analysis of the resin by a temperature increase, to lower temperatures.

In addition, it is preferred that the evaluating the resin be performed based on a temperature difference between the characteristic peak and a peak except the characteristic peak.

In addition, the resin may be a resin having a side chain having a nitrogen-containing aromatic ring group and a crosslinking portion.

The resin may be a catalyst obtained by causing a crosslinked vinylpyridine resin to carry a rhodium complex, the catalyst being used as a catalyst in a method of producing acetic acid through a methanol carbonylation reaction.

According to another embodiment of the present invention, there is provided a method of evaluating a resin, the method including: heating the resin to cause depolymerization resulting from random scission of a main chain of the resin; measuring a temperature of the resin at which the depolymerization occurs; and evaluating a deterioration degree of the resin based on the measured temperature.

Further features of the present invention will become apparent from the following description of exemplary embodiments with reference to the attached drawings.

DESCRIPTION OF THE EMBODIMENTS

A method of evaluating a resin of the present invention includes evaluating the resin based on the shift of a characteristic peak representing the deterioration degree of the resin, the peak being observed in the thermal analysis of the resin by a temperature increase, to lower temperatures.

The resin to be evaluated is, for example, a resin having a side chain having a nitrogen-containing aromatic ring group and a crosslinking portion. The resin having a side chain having the nitrogen-containing aromatic ring group and the crosslinking portion is a resin that causes main chain cleavage-type thermal decomposition. Examples of the nitrogen-containing aromatic ring group include a group formed of a nitrogen-containing six-membered ring such as pyridine, a group formed of a nitrogen-containing five-membered ring such as pyrrole, and a group formed of a nitrogen-containing fused ring such as pyrrolidine. In addition, examples of the crosslinking portion include structures derived from various crosslinkable monomers each having two or more groups including ethylenically unsaturated bonds. In addition, the structure of the main chain, which is not particularly limited, is, for example, a polyvinyl.

The resin having aside chain having the nitrogen-containing aromatic ring group and the crosslinking portion is specifically, for example, a polymer of a crosslinked pyridine resin such as a copolymer of 4-vinylpyridine including a pyridine ring whose nitrogen atom can be quaternized in its structure and divinylbenzene. In addition, polymers including, instead of 4-vinylpyridine described above, various basic nitrogen-containing monomers, e.g., 2-vinylpyridine the position of the vinyl group of which is different from that of 4-vinylpyridine, substituted vinylpyridines such as vinyl methylpyridine, and vinylquinolines, and polymers including, instead of divinylbenzene, various crosslinkable monomers each having two or more groups including ethylenically unsaturated bonds can each be used. Further, polymers including other polymerizable comonomers such as styrene and methyl acrylate in addition to the basic nitrogen-containing monomers and the crosslinkable monomers can each be used.

Although the resin having the crosslinking portion has been given as an example of the resin to be evaluated, a resin free of any crosslinking portion is also permitted.

Examples of the thermal analysis include thermogravimetry (TG), thermogravimetry-mass spectrometry (TG-MS), and derivative thermogravimetry (DTG). In the thermal analysis to be performed in the evaluation method of the present invention, it is essential to observe the behavior of the resin while increasing its temperature. The performance of such thermal analysis enables the determination of a change in amount of the thermal decomposition product of the resin such as a structure derived from the nitrogen-containing aromatic ring group or a structure derived from the crosslinking portion.

In the thermal analysis, the characteristic peak representing the deterioration degree of the resin (hereinafter sometimes simply referred to as "characteristic peak"), which is described in detail later, is a peak except a peak to be finally observed out of the peaks representing depolymerization resulting from the random scission of the main chain to be observed in a temperature increase process. Therefore, a peak representing the depolymerization of a main chain terminal to be observed at a temperature lower than those of the peaks representing the depolymerization resulting from the random scission of the main chain in the temperature increase process is not the characteristic peak. The inventors have found that the characteristic peak has such a characteristic that as the decomposition (deterioration) of the resin progresses, its peak top temperature moves, i.e., shifts to lower temperatures, and the shift to lower temperatures correlates with the decomposition ratio of the resin.

In addition, the inventors have found that a difference between the peak top temperature of a certain characteristic peak and the peak top temperature of a peak that shifts to lower temperatures to a smaller extent than that of the characteristic peak does or hardly shifts correlates with the decomposition ratio of the resin. In particular, there is an extremely high correlation between: a difference between the peak top temperature of a peak whose peak top temperature is hardly changed by the decomposition unlike the characteristic peak (hereinafter sometimes referred to as "reference peak") and the peak top temperature of the characteristic peak; and the decomposition ratio.

Therefore, the decomposition ratio of the resin can be quantitatively determined with ease and high accuracy as described below. Resins having various decomposition ratios are produced by using the same resin (e.g., the same product) as the object of evaluation, and a relationship between information based on the shift of the characteristic peak to lower temperatures (e.g., the peak top temperature of the characteristic peak or a difference in peak top temperature between the characteristic peak and any other peak) and a decomposition ratio is determined in advance by subjecting the resins to thermal analysis by a temperature increase. Information about the characteristic peak is acquired by subjecting the resin to be evaluated to thermal analysis by a temperature increase, and the decomposition ratio is determined by using the relationship between the information based on the shift of the characteristic peak to lower temperatures and the decomposition ratio determined in advance.

In addition, in the case of a resin to be used in an application in which a deteriorated resin needs to be, for example, exchanged or recycled such as a reaction catalyst, the following threshold control can be performed: the resin is exchanged or recycled when the information based on the characteristic peak of the resin to be evaluated exceeds, or falls short of, a predetermined value judging from the relationship between the information based on the characteristic peak and the decomposition ratio determined in advance.

Figure 1:
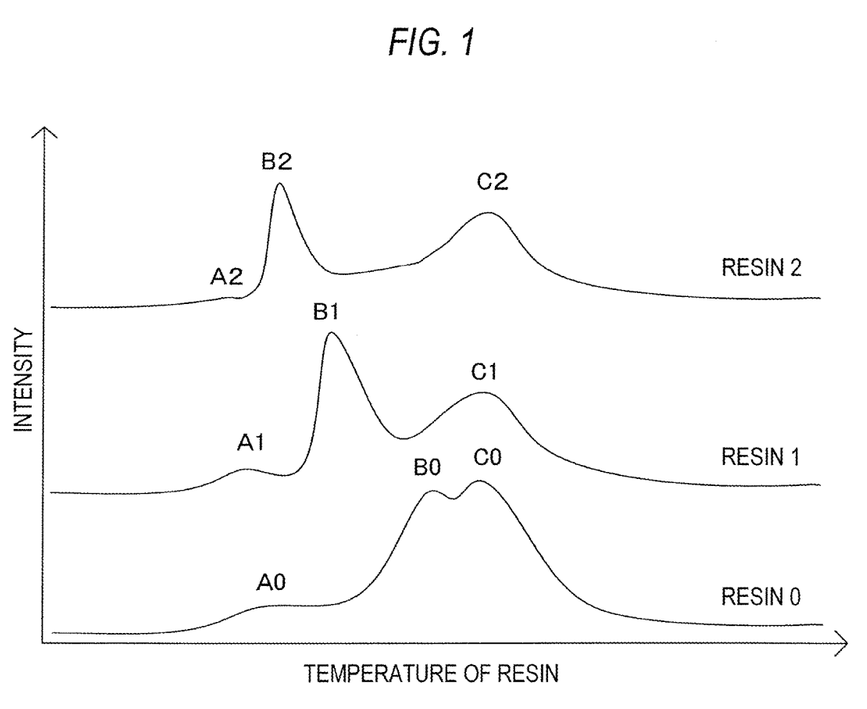
FIG. 1 is a graph showing the outline of a peak to be observed in thermal analysis.
Figure 2:
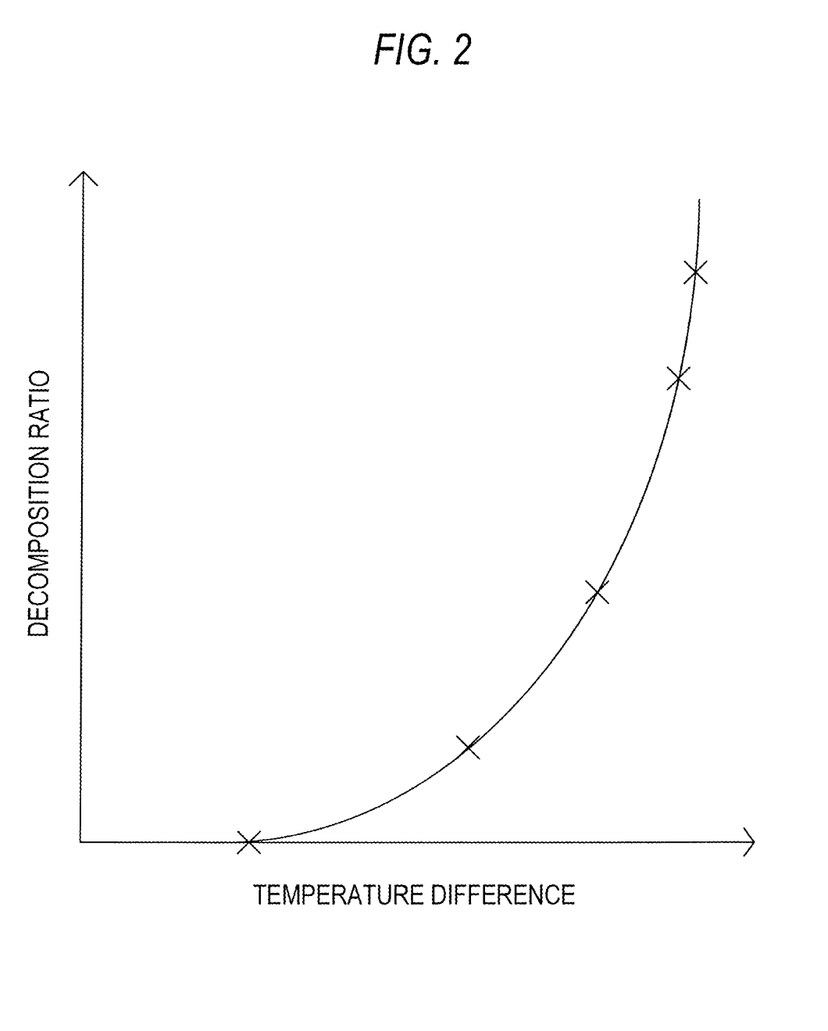
FIG. 2 is a graph showing a relationship between a difference in peak top temperature between two predetermined peaks and the decomposition ratio of a resin.

Behavior that occurs when the resin to be evaluated is subjected to thermal analysis and its evaluation are described below with reference to FIG. 1 and FIG. 2 by taking, as an example of the resin to be evaluated, a product obtained by quaternizing a polyvinylpyridine resin crosslinked with divinylbenzene with methyl iodide and causing the resultant to carry rhodium, the product being used as a catalyst in a production method for acetic acid through the carbonylation of methanol. FIG. 1 is a graph showing the outline of a peak to be observed in the thermal analysis. The axis of abscissa of FIG. 1 indicates the temperature of the resin, and an intensity indicated by the axis of ordinate of FIG. 1 corresponds to the amount of released vinylpyridine and ethylbenzene. FIG. 2 is a graph showing a relationship between: a difference in peak top temperature between two predetermined peaks as information based the shift of the characteristic peak to lower temperatures; and the decomposition ratio of the resin.

When an unused resin 0 that has not deteriorated or decomposed is heated in the thermal analysis, first, $CH_3I$ (m/z=142) bonded to a pyridine group on a side chain desorbs at from 190° C. to 320° C. (not shown).

Next, when the temperature exceeds 300° C., vinylpyridine (m/z=105) as a monomer is released from a main chain terminal. The depolymerization of the main chain terminal is observed as a peak A0. The depolymerization of the main chain terminal has no relevance to deterioration due to thermal decomposition and the random scission of the main chain is not involved therein.

When the resin is heated to additionally high temperature, its main chain randomly cleaves, and vinylpyridine (m/z=105) and ethyl vinyl benzene (m/z=132) as monomers are released from the respective end portions produced by the cleavage. Ethyl vinyl benzene is a structure derived from the crosslinking portion. The temperature range of the depolymerization resulting from the random scission of the main chain becomes relatively wide (320° C. to 500° C.) because of the molecular weight distribution and crosslinking degree distribution of the resin, and the depolymerization is observed as a peak B0 appearing near the temperature of its start and a peak C0 appearing near the temperature of its ending. That is, in the depolymerization resulting from the random scission of the main chain, the peak (B0) at which vinylpyridine and ethyl vinyl benzene start to desorb, and the peak (C0) at which the desorption ends are observed. It should be noted that the depolymerization is the reverse reaction of polymerization and means that a polymerized substance decomposes by virtue of the action of heat or the like to turn into a monomer.

On the other hand, when a resin used as a catalyst, i.e., a resin 1 that has decomposed is heated in the thermal analysis, first, $CH_3I$ bonded to a pyridine group on a side chain desorbs at from 190° C. to 320° C. (not shown).

Next, when the temperature exceeds 300° C., as in the resin 0, vinylpyridine as a monomer is released from a main chain terminal. The depolymerization of the main chain terminal is observed as a peak A1.

When the resin is further heated, as in the resin 0, its main chain randomly cleaves, and vinylpyridine and ethyl vinyl benzene as monomers are released from the respective end portions produced by the cleavage. Ethyl vinyl benzene is a structure derived from the crosslinking portion. The temperature range of the depolymerization resulting from the random scission of the main chain becomes relatively wide because of the molecular weight distribution and crosslinking degree distribution of the resin, and the depolymerization is observed as a peak B1 appearing near the temperature of its start and a peak C1 appearing near the temperature of its ending.

The peak top temperature of the peak B1 at which vinylpyridine and ethyl vinyl benzene start to desorb in the depolymerization resulting from the random scission of the main chain shifts to lower temperatures as compared to the peak B0 of the unused resin 0. On the other hand, the peak top temperature of the peak C1 at which the desorption of vinylpyridine and ethyl vinyl benzene ends in the depolymerization resulting from the random scission of the main chain is substantially equal to that of the peak C0 of the unused resin 0.

In addition, when a resin 2 that has additionally decomposed as compared to the resin 1 is heated in the thermal analysis, first, $CH_3I$ bonded to a pyridine group on a side chain desorbs at 190° C. to 320° C. (not shown).

Next, when the temperature exceeds 300° C., as in the resin 0 and the resin 1, vinylpyridine as a monomer is released from a main chain terminal. The depolymerization of the main chain terminal is observed as a peak A2.

When the resin is heated to additionally high temperature, as in the resin 0 and the resin 1, its main chain randomly cleaves, and vinylpyridine and ethyl vinyl benzene as monomers are released from the respective end portions produced by the cleavage. Ethyl vinyl benzene is a structure derived from the crosslinking portion. The temperature range of the depolymerization resulting from the random scission of the main chain becomes relatively wide because of the molecular weight distribution and crosslinking degree distribution of the resin, and the depolymerization is observed as a peak B2 appearing near the temperature of its start and a peak C2 appearing near the temperature of its ending.

The peak top temperature of the peak B2 at which vinylpyridine and ethyl vinyl benzene start to desorb in the depolymerization resulting from the random scission of the main chain shifts to additionally lower temperatures as compared to the peak B1 of the resin 1. In addition, the peak top temperature of the peak C2 at which the desorption of vinylpyridine and ethyl vinyl benzene ends in the depolymerization resulting from the random scission of the main chain is substantially equal to that of the peak C1 of the resin 1.

In other words, a difference in peak top temperature between the peak at which vinylpyridine and ethyl vinyl benzene start to desorb in the depolymerization resulting from the random scission of the main chain, and the peak at which the desorption of vinylpyridine and ethyl vinyl benzene ends in the depolymerization resulting from the random scission of the main chain enlarges as the deterioration and decomposition progress.

The peak B0, B1, or B2 that represents the depolymerization resulting from the random scission of the main chain and shifts to lower temperatures as the resin decomposes as described above is the characteristic peak representing the deterioration degree of the resin. The peak A0, A1, or A2 representing the depolymerization of the main chain terminal not resulting from the random scission of the main chain, and the peak C0, C1, or C2 at which the desorption ends in the depolymerization resulting from the random scission of the main chain are not characteristic peaks.

It should be noted that the depolymerization of the main chain terminal occurs only from the main chain terminal. Accordingly, the intensity of the peak A0, A1, or A2 representing the depolymerization of the main chain terminal is extremely weak as compared to that of the peak B0, B1, or B2 representing the depolymerization resulting from the random scission of the main chain, and hence the peaks can be clearly distinguished from each other.

The reason why the plurality of peaks (B0, B1, B2, C0, C1, and C2) representing the depolymerization resulting from the random scission of the main chain appear, and the peaks (B0, B1, and B2) at low temperatures shift to lower temperatures as the decomposition of the resin progresses is assumed to be as described below. A cause for the appearance of the plurality of peaks representing the depolymerization is the fact that the resin itself has a molecular weight distribution and a crosslinking degree distribution, and a portion having a relatively strong bond and a portion having a relatively weak bond are present in the resin, and hence the portion having a relatively weak bond desorbs at low temperature and the portion having a relatively strong bond desorbs at high temperature.

Then, as the decomposition of the resin progresses, the crosslinking portion is, for example, cut, and hence the crosslinked structure of the resin loosens, the nonuniformity of the structure rises, the number of thermally unstable terminal unsaturated bonds or branches increases, and the desorption is likely to occur. Accordingly, the structure of the portion having a relatively weak bond is additionally likely to loosen and the desorption is extremely likely to occur. Therefore, the desorption of the portion having a relatively weak bond is assumed to shift to even lower temperatures.

The shift of the characteristic peak to lower temperatures that occurs as the decomposition of the resin progresses correlates with the decomposition ratio of the resin. For example, when a temperature difference between the characteristic peak (B0, B1, B2, or the like) as a peak at which desorption starts in depolymerization resulting from the random scission of the main chain of each of resins having different decomposition ratios and the peak (C0, C1, C2, or the like) at which the desorption ends in the depolymerization resulting from the random scission of the main chain, the peaks C0, C1, C2, and the like having substantially the same peak top temperature, is plotted against the decomposition ratio of the resin as shown in FIG. 2, a graph in which the difference and the decomposition ratio extremely correlate with each other can be obtained.

Therefore, the deterioration degree of the resin to be evaluated can be quantitatively determined with ease and high accuracy as described below. Resin samples having different decomposition ratios are produced by using the same resin (e.g., the same product resin) as the object of evaluation, and a relationship between information based on the shift of the characteristic peak to lower temperatures (e.g., the peak top temperature of the characteristic peak or a difference in peak top temperature between the characteristic peak and any other peak) and a decomposition ratio is determined in advance by subjecting the samples to thermal analysis by a temperature increase. Information about the characteristic peak is acquired by subjecting the resin to be evaluated to thermal analysis, and the deterioration degree is determined by using the relationship between the information based on the shift of the characteristic peak to lower temperatures and the decomposition ratio determined in advance. Although a method involving evaluating the deterioration degree of the resin based on a change in chemical structure of the resin through an infrared absorption spectrum (IR), a nuclear magnetic resonance method (NMR), Raman spectroscopy, or the like, or a method involving evaluating the deterioration degree of the resin based on changes in physical characteristics such as a tension test is conceivable as a method of evaluating the deterioration degree of the resin, the evaluation method of the present invention has higher accuracy and higher facility than those of any such evaluation method.

Although the method of evaluating the resin based on the characteristic peak observed in the thermal analysis by a temperature increase has been described above, the resin can also be evaluated, for example, as described below. The resin is heated to cause depolymerization resulting from the random scission of the main chain of the resin, the temperature of the resin at which the depolymerization occurs is measured, and the evaluation is performed based on the measured temperature. As described in the foregoing, there is a correlation between the deterioration degree of the resin and the temperature of the resin at which the depolymerization resulting from the random scission of the main chain of the resin, the depolymerization being caused by the heating, occurs. That is, as the deterioration of the resin progresses, the bond of the main chain of the resin weakens, and hence the main chain of the resin randomly cleaves and the depolymerization occurs at lower temperature. Therefore, the decomposition ratio of the resin can be quantitatively determined with ease and high accuracy as described below. Resins having different deterioration degrees are produced by using the same resin as the object of evaluation, each of the resins is heated to cause depolymerization resulting from the random scission of the main chain of the resin, and a relationship between the temperature of the resin at which the depolymerization resulting from the random scission of the main chain of the resin occurs and a decomposition ratio is determined in advance. The resin to be evaluated is heated, the temperature of the resin at which depolymerization resulting from the random scission of its main chain occurs is measured, and the decomposition ratio is determined by using the relationship between the temperature of the resin at which the depolymerization resulting from the random scission of the main chain of the resin occurs and the decomposition ratio determined in advance. For example, the deterioration degree of the resin can be evaluated with ease and high accuracy by: observing the external appearance of the resin with a microscope or the like; judging the depolymerization resulting from the random scission of the main chain of the resin; and determining the temperature of the resin at which the depolymerization resulting from the random scission of the main chain of the resin occurs.

The temperature at which the depolymerization resulting from the random scission of the main chain to be measured occurs only needs to be appropriately specified depending on a change in the resin caused by the depolymerization resulting from the random scission of the main chain of the resin and a measurement method or an observation method. For example, when the color of the resin changes as a result of the depolymerization resulting from the random scission of the main chain, the temperature of the resin at which the color becomes a predetermined color is measured through external appearance observation. For example, in the thermal analysis, the starting temperature of the characteristic peak, the peak top temperature of the characteristic peak, or the like may be defined as the temperature at which the depolymerization occurs. At the peak top temperature of the characteristic peak observed in the thermal analysis, its intensity is high, i.e., a large amount of a monomer is released, and hence it can be said that a large change occurs in the external appearance observation as well and a change in color, shape, or the like is easily observed.

It should be noted that in the case of an ion exchange resin or the like, an exchange group such as a sulfo group ($-SO_3H$) desorbs from the resin, and hence the performance of the ion exchange resin deteriorates, and the resin needs to be exchanged or recycled. Therefore, the application of the evaluation method of the present invention, which is an evaluation method based on the decomposition phenomenon of a resin that occurs at a temperature higher than that of the desorption of the exchange group, to the ion exchange resin has little significance.

In addition, when an electronegative group is present on a side chain of a resin like polyvinyl chloride (PVC), the group reacts with a hydrogen atom or the like in its main chain adjacent to the group at a temperature lower than that of the cleavage of the main chain to desorb a stable compound (Rx), and hence the resin deteriorates. Therefore, the application of the evaluation method of the present invention to a resin having an electronegative group on a side chain thereof also has little significance.

That is, it is basically preferred that the evaluation method of the present invention be applied to a resin to be used until the cutting or cleavage of the main chain or crosslinking portion thereof occurs.

As described above, a resin that can be suitably evaluated by the method of evaluating a resin of the present invention is applied to, for example, a catalyst for a production method for acetic acid through the carbonylation of methanol. A method of carbonylating methanol in the presence of the catalyst includes, for example, a reaction step of causing methanol (carbonylation raw material) to react with carbon monoxide in a liquid phase including a solid catalyst, which is obtained by causing a resin carrier containing quaternized nitrogen to carry a precious metal complex on itself, to produce acetic acid (carbonyl compound), a distillation step of distilling a reaction product liquid coming from the reaction step to recover a vapor phase fraction including acetic acid (carbonyl compound), and a circulation step of circulating a bottom product coming from the distillation step to the reaction step.

Figure 3:
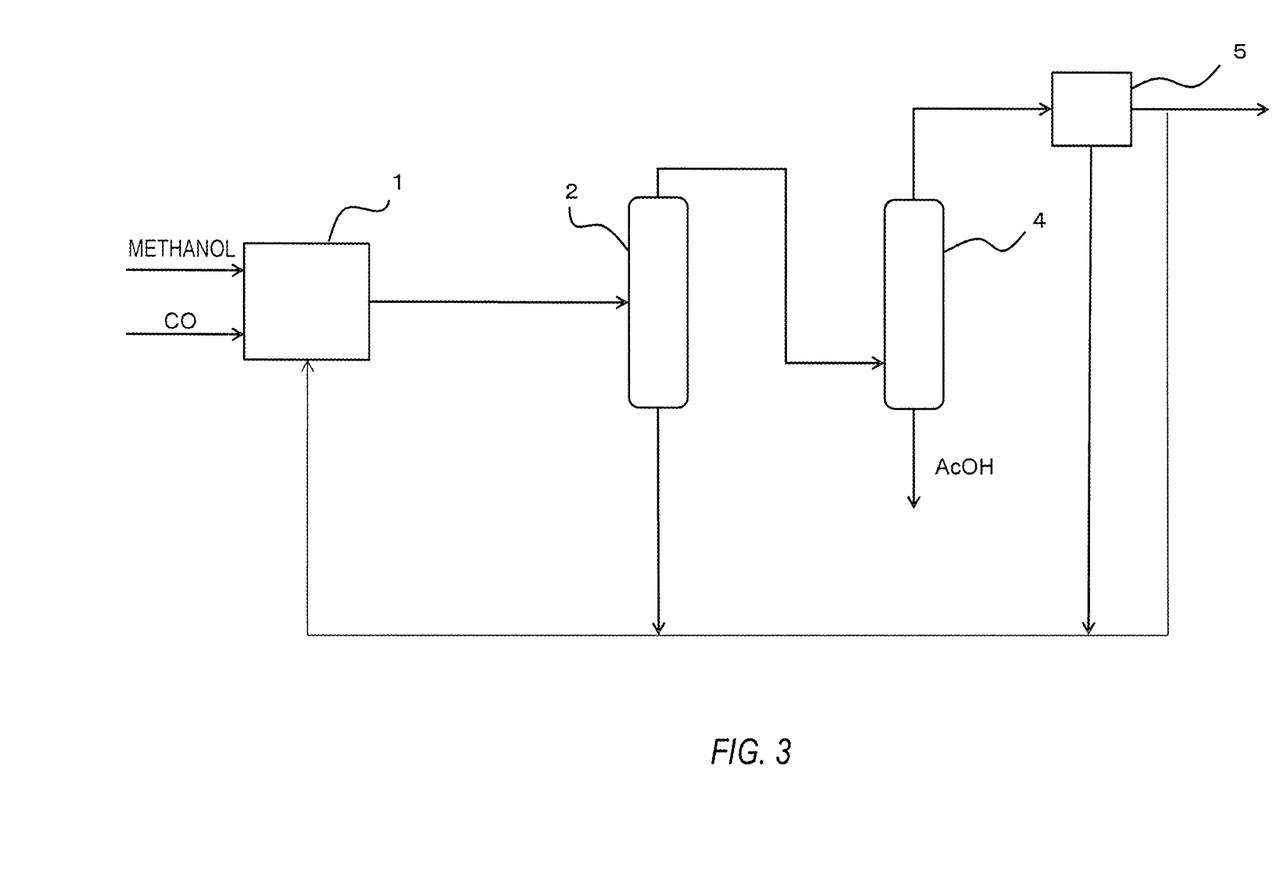
FIG. 3 is a schematic view illustrating an example of an acetic acid-producing apparatus.

FIG. 3 is a schematic view of an acetic acid-producing apparatus capable of performing the production of acetic acid through the carbonylation of methanol. As illustrated in FIG. 3, the acetic acid-producing apparatus mainly includes: a carbonylation reactor 1 as the reaction step; a flasher 2 for performing a flash evaporation step and a light end distillation column 4 for performing a light end separation step as the distillation step; and a decanter 5 as a standing step.

Methanol as a carbonylation raw material and carbon monoxide are introduced into the carbonylation reactor 1. Acetic acid as a reaction solvent circulates between the carbonylation reactor 1 and the flasher 2. The bottom product of the flasher 2 formed mainly of acetic acid is adapted to return to the carbonylation reactor 1. A vapor phase fraction coming from the flasher 2 flows into the light end distillation column 4 and is separated in the light end distillation column 4. Acetic acid is separated and recovered from the lower portion of the light end distillation column 4, and a component except acetic acid and a portion that has not been recovered out of acetic acid are distilled out of the apex portion thereof.

Present in the carbonylation reactor 1 is a solid catalyst formed of a resin carrier containing quaternized nitrogen and a precious metal complex carried by the resin carrier through ion exchange, the solid catalyst being dispersed in a liquid phase. The resin carrier constituting the solid catalyst is a resin to be evaluated by the method of evaluating a resin of the present invention.

The resin carrier containing the quaternized nitrogen is typically a pyridine resin, i.e., a resin including a pyridine ring whose nitrogen atom can be quaternized in its structure, and a representative example thereof is a copolymer of 4-vinylpyridine and divinylbenzene. It should be noted that the resin carrier is not limited to the specific resin and is meant to comprehensively include a resin containing basic nitrogen that can be quaternized to adsorb and carry the precious metal complex. Therefore, polymers including, instead of 4-vinylpyridine described above, various basic nitrogen-containing monomers, e.g., 2-vinylpyridine the position of the vinyl group of which is different from that of 4-vinylpyridine, substituted vinylpyridines such as vinyl methylpyridine, and vinylquinolines, and polymers including, instead of divinylbenzene, various crosslinkable monomers each having two or more groups including ethylenically unsaturated bonds can each be used. Further, polymers including other polymerizable comonomers such as styrene and methyl acrylate in addition to the basic nitrogen-containing monomers and the crosslinkable monomers can each be used.

The crosslinking degree of the resin carrier (determined by representing the content of a crosslinkable monomer in a wt % unit) is preferably 10% or more, more preferably from 15 to 40%. When the crosslinking degree is lower than 10%, the swelling or contraction of the resin carrier due to the composition of the liquid phase becomes remarkable, and when the crosslinking degree is excessively high, the content of the basic nitrogen for carrying the precious metal complex becomes excessively small. The content of the basic nitrogen in the resin only needs to be from about 2 to 10 milliequivalents per gram in terms of a basic equivalent, and is more preferably from 3.5 to 6.5 milliequivalents per gram. The basic nitrogen, which can be generally present in a form such as a free base form, an acid-added salt form, or an N-oxide form, adsorbs and carries the precious metal complex in an ion exchange manner in a state of being quaternized. The resin carrier is typically used in the form of a spherical particle, and its particle diameter is generally from 0.01 to 2 mm, preferably from 0.1 to 1 mm, more preferably from 0.25 to 0.7 mm.

The precious metal complex to be carried by the resin carrier is a complex of a precious metal showing a catalytic action on a carbonylation reaction, and is adsorbed by the quaternized nitrogen of the resin carrier in an ion exchange manner. Although rhodium and iridium have each been known as such precious metal, in general, rhodium is suitably used. When the resin carrier and a halide of rhodium or a rhodium salt such as rhodium acetate are brought into contact with each other in a solution containing methyl iodide under pressure of carbon monoxide (0.7 to 3 MPa), the resin carrier can be caused to carry rhodium. At this time, a nitrogen atom in the resin carrier is quaternized, and a rhodium complex ion produced by a reaction among the rhodium halide, methyl iodide, and carbon monoxide, i.e., a rhodium carbonyl complex $[Rh(CO)_2I_2]^-$ adsorbs to the atom in an ion exchange manner. Thus, the solid catalyst to be used is obtained.

Methanol reacts with carbon monoxide to produce acetic acid. At this time, a reaction accelerator such as methyl iodide is suitably added. Although the reaction is typically performed by using acetic acid as a reaction solvent, in this case, acetic acid serves not only as the reaction product but also as the reaction solvent. For example, a carbon monoxide gas is blown into a reaction liquid in the carbonylation reactor 1 having dispersed therein the solid catalyst, and methanol reacts with carbon monoxide in the presence of the rhodium complex-carrying solid catalyst under the conditions of a reaction temperature of from 100° C. to 200° C. and a reaction pressure of from about 1 to 5 MPa to produce acetic acid. In the reaction, methyl acetate, dimethyl ether, water, and the like are produced as reaction byproducts, and these byproducts are returned as a residual liquid from which acetic acid has been separated and recovered as a product to the reaction step together with the solvent, the reaction accelerator, and an unreacted raw material. Accordingly, the liquid phase in the reaction step is formed of a mixture of all of those components.

The reaction product liquid produced in the reaction step is subjected to a separation operation in the subsequent distillation step, produced acetic acid is separated and recovered as a product, and part of the residual liquid except the product is returned to the reaction step and the remainder proceeds to the standing step. For example, the reaction liquid is taken out of the carbonylation reactor 1 as the reaction step through a screen or the like and flows into the flasher 2. In the distillation step, the following approach is adopted: first, part of the reaction liquid is vaporized in the flasher 2 to be separated into a vapor phase and a liquid phase (flash evaporation step), and then the vapor phase fraction is introduced from the upper portion of the flasher 2 into the light end distillation column 4, and acetic acid is separated and recovered from the lower portion thereof (light end separation step). It is because of the following reason that such approach is adopted: the reaction product liquid is a mixture of various components as described above and acetic acid is a component having a small degree of volatility out of the components, but in actuality, an impurity that has a smaller degree of volatility (or is nonvolatile) is included and hence acetic acid cannot be recovered as the product from the bottom product. The flasher 2 and the light end distillation column 4 can be configured as separate towers as illustrated in FIG. 3, or can be integrally provided in the bottom portion and upper portion of a single column. It should be noted that the carbonylation reaction is generally an exothermic reaction, and hence vaporizing the part in the flasher 2 exhibits a cooling effect on the liquid phase fraction to be returned to the reaction step and introducing the heated reaction product liquid into the flasher 2 can cause the flasher to function as an evaporator for the light end distillation column 4.

In the light end distillation column 4, the vapor phase fraction is separated. When part of acetic acid having the smallest degree of volatility out of the components constituting the vapor phase fraction is adapted to accumulate in the lower portion of the light end distillation column 4, all other vapor phase components can be adapted to be incorporated into an overhead fraction. Acetic acid is taken out of the lower portion of the light end distillation column 4 and subjected to necessary purification treatment, and is then separated and recovered as a product. On the other hand, an effluent from the overhead is introduced into the decanter 5.

The overhead effluent of the light end distillation column 4 to be introduced into the decanter 5 after the separation of acetic acid in the distillation step contains methyl iodide, methyl acetate, and water as main components. When the effluent is left at rest in the decanter 5, methyl iodide in the effluent is separated as a heavy oil phase and an aqueous phase is obtained. Methyl iodide thus separated is adapted to return to the carbonylation reactor 1.

In addition, a portion that has not been vaporized in the flasher 2 accumulates as a liquid phase fraction in the bottom portion of the flasher 2 and is returned as a bottom product coming from the distillation step (i.e., a liquid phase fraction coming from the flasher 2) to the carbonylation reactor 1 for performing the reaction step.

When the catalyst resin to be used in the production method for acetic acid is evaluated by employing the method of evaluating a resin of the present invention, its deterioration degree can be quantitatively evaluated with high accuracy and ease, and hence the timing at which the resin is exchanged or recycled can be identified. Therefore, acetic acid can be efficiently produced. Although the production of acetic acid has been described above, a carbonyl compound except acetic acid can also be produced by replacing methanol with any other carbonylation raw material.

The present invention is described below by way of Examples for a further understanding thereof. However, the present invention is by no means limited to Examples.

<Production of Rhodium-Carrying Catalyst>

A crosslinked vinylpyridine resin carrier was produced by a suspension polymerization method. Specifically, first, a liquid obtained by dissolving 625 g of NaCl (specific gravity adjustor), 18.8 g of $NaNO_2$ (radical scavenger), 4.2 g of gelatin (oil droplet stabilizer), and 0.5 g of sodium dodecylbenzenesulfonate (surfactant) in 5,241 g of ion-exchanged water was prepared as an aqueous phase.

In addition, 1,364 g of 4-vinylpyridine (vinylpyridine-based monomer) and 1,636 g (such an amount that a crosslinking degree became 30%) of divinylbenzene (purity: 56 to 57 wt %, with the balance being ethyl vinyl benzene) (crosslinking agent) were mixed, and 562 g of toluene (pore-forming agent), 188 g of octane (pore-forming agent), 25.2 g of benzoyl peroxide (polymerization initiator), and 10.2 g of 2,2'-azobis(2,4-dimethylvaleronitrile) (auxiliary polymerization initiator) were dissolved in the mixture to prepare an oil phase. It should be noted that the crosslinking degree is determined by the following equation.

Crosslinking degree (%)=$A/B$×100

A: The mass of a crosslinking agent in a resin
B: The mass of a vinylpyridine-based monomer The prepared oil phase was charged into a 10-L suspension polymerization reactor with a jacket. The prepared aqueous phase was supplied from the lower portion of the reactor to the oil phase and the mixture was gently stirred. After the mixture had been stirred until oil droplets were uniformly dispersed, warm water at 65° C. was flowed through the jacket of the reactor to increase the temperature of the liquid in the reactor and the monomers were polymerized in the reactor. After the temperature of the liquid in the reactor had increased to 60° C., its increase rate increased, and after the temperature had increased to 80° C., the temperature gradually reduced. After it had been confirmed that the temperature of the liquid in the reactor had reduced to 60° C., the temperature of the liquid in the reactor was further increased to 90° C. and held as it was for 4 hours. After that, the liquid in the reactor was cooled to normal temperature and subjected to solid-liquid separation by filtration to provide a spherical resin. The pore-forming agents (toluene and octane) were removed from the resultant spherical resin, and the remainder was classified into a product having a diameter of from 0.2 to 0.8 mm with a sieve. Thus, a porous vinylpyridine resin (crosslinked vinylpyridine resin carrier) was obtained. The resultant crosslinked vinylpyridine resin has a crosslinking degree of 30%.

51 Grams (on a dry-resin basis) of the vinylpyridine resin were loaded into a reactor and water was sufficiently drained. After that, 102 g of methyl iodide and 378 g of acetic acid were added to quaternize the resin at room temperature.

A predetermined amount of rhodium acetate was loaded into the reactor, and rhodium was turned into a complex $[Rh(CO)_2I_2]^-$ by heating rhodium acetate to a temperature of from 130° C. to 180° C. while blowing carbon monoxide into the reactor. The complex was immobilized to a quaternized pyridine group through an ion exchange reaction to provide a rhodium-carrying catalyst. The carrying amount of rhodium was 0.85 wt % with respect to the carrier before the quaternization (crosslinked vinylpyridine resin carrier).

<Production of Catalyst Samples Having Different Decomposition Ratios by Accelerated Thermal Decomposition Test>

(Preparation of Sample 1)

8.5 Grams (on a dry-resin basis) of the rhodium-carrying catalyst obtained in the section <Production of rhodium-carrying catalyst> were weighed and loaded into a 200-mL metal autoclave together with 100 mL of a model liquid (composition: 5.5 wt % of $H_2O$, 8.0 wt % of $CH_3I$, and 86.5 wt % of $CH_3COOH$). The rhodium-carrying catalyst was decomposed by heating the mixture at 220° C. for 27 hours while stirring the mixture under a nitrogen atmosphere. After that, the autoclave was cooled to room temperature, a reaction liquid and the decomposed rhodium-carrying catalyst were separated from each other, the concentration of a nitrogen-containing compound in the reaction liquid was measured, and the decomposition ratio of the resin as a carrier for the rhodium-carrying catalyst was determined by the following equation. As a result, the decomposition ratio was 0.7%. In addition, the decomposed rhodium-carrying catalyst separated from the reaction liquid was washed with methanol and fractionated from methanol. After that, methanol taken in the pores of the resin of the rhodium-carrying catalyst was volatilized by leaving the catalyst to stand overnight. After that, the residue was dried at 105° C. for 48 hours to provide a sample for TG analysis (sample 1).

Decomposition ratio (%)=amount (g) of nitrogen-containing compound produced by decomposition/amount (g) of raw material pyridine group×100

(Preparation of Samples 2 to 5)

The same operations as those of the sample 1 were performed except that the heating at 220° C. for 27 hours was changed to heating at 220° C. for 46 hours (sample 2), heating at 220° C. for 48 hours (sample 3), heating at 220° C. for 96 hours (sample 4), or heating at 220° C. for 144 hours (sample 5). It should be noted that the sample 2 had a decomposition ratio of 9.2%, the sample 3 had a decomposition ratio of 10.3%, the sample 4 had a decomposition ratio of 23.0%, and the sample 5 had a decomposition ratio of 28.0%.

<TG-MS Analysis>

Figure 4:
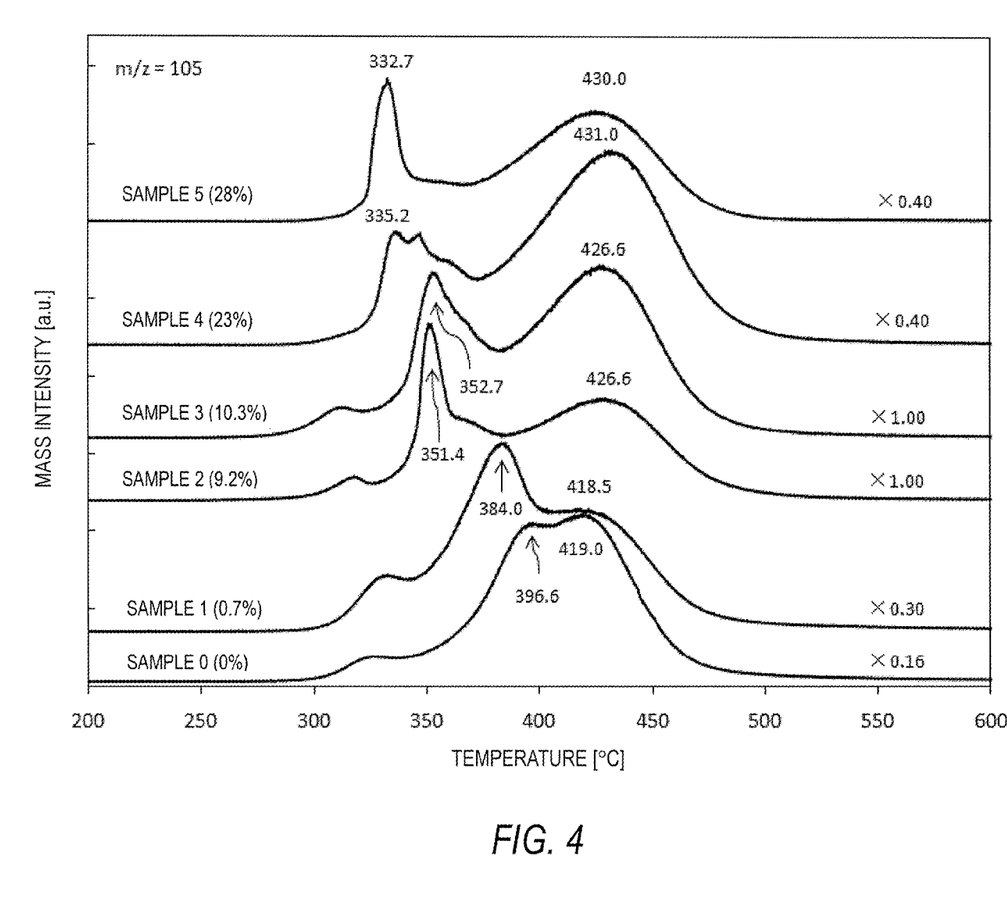
FIG. 4 is a graph showing the profiles of samples 0 to 5 at an m/z of 105.
Figure 5:
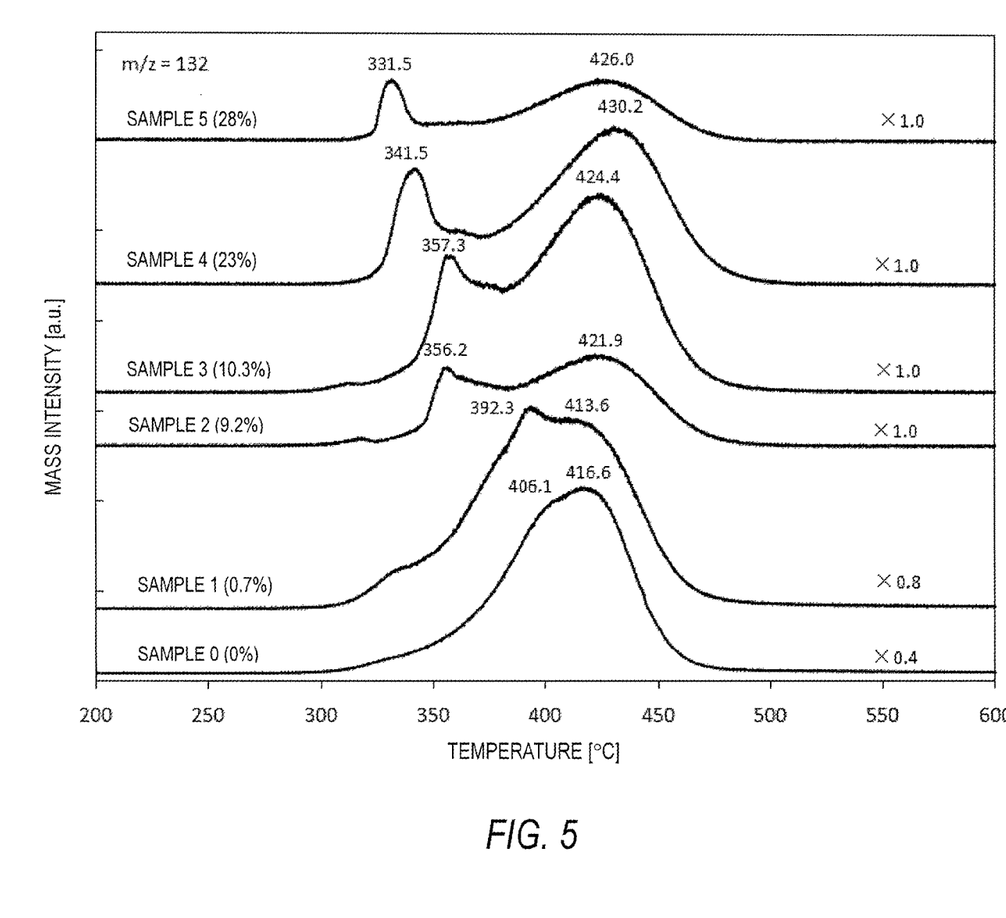
FIG. 5 is a graph showing the profiles of the samples 0 to 5 at an m/z of 132.

The resultant samples 1 to 5 and the rhodium-carrying catalyst (sample 0) obtained in the section <Production of rhodium-carrying catalyst> were each subjected to TG-MS analysis with a TG-MS apparatus (obtained by directly coupling a TG apparatus with an MS apparatus). Specifically, about 3.5 mg of each sample were weighed and mounted on a TG cell, and its temperature was increased from 25° C. to 600° C. at a rate of 20° C./min while a He gas was flowed at 100 mL/min. A decomposition product produced in the temperature increase process was introduced from a TG-MS interface portion into the ionization chamber of the MS together with the He gas. The decomposition product was ionized in the ionization chamber and subjected to mass analysis with a quadrupole electrode. FIG. 4 shows the resultant TG-MS profiles at an m/z of 105. In addition, FIG. 5 shows the resultant TG-MS profiles at an m/z of 132. Temperatures indicated by the axes of abscissa of FIG. 4 and FIG. 5 are the temperatures of resins. The profiles shown in FIG. 4 and FIG. 5 are multiplied by certain magnifications in order that their intensities (mass intensities) may be uniformized, and a multiplied magnification is represented by "×numerical value". It should be noted that an m/z of 105 is the peak of a vinylpyridine molecular ion and an m/z of 132 is the peak of an ethyl vinyl benzene molecular ion.

<Analysis of TG-MS Profile>

As shown in FIG. 4 and FIG. 5, two peaks were mainly observed in each of the samples 0 to 5. In addition, a peak at the lower temperature out of the two peaks shifted to lower temperatures as the decomposition ratio increased. In addition, at a temperature lower than those of the two peaks, a peak extremely small as compared to the two peaks was observed.

The foregoing is described in detail. When the sample 0 as a carrier resin that had not decomposed was heated, $CH_3I$ (m/z=142) desorbed from a quaternized pyridine ring at 180° C. to 300° C. (not shown). In addition, when the temperature exceeded 300° C., vinylpyridine (m/z=105) and ethyl vinyl benzene (m/z=132) started to be produced together with $CH_3I$, and their amount peaked at 322° C. This is probably because the depolymerization of a polymer main chain terminal in the carrier resin occurred to release vinylpyridine and ethyl vinyl benzene. It should be noted that it is assumed that the random scission of the polymer main chain that can occur in a deterioration process is not involved in the depolymerization at the temperature. Further, when the sample was heated to 330° C. or more, the polymer main chain randomly cleaved, and such depolymerization that the monomers were released from the respective end portions produced by the random scission started and continued until the temperature reached 500° C. It is assumed that the sample 0 as the carrier resin that had not decomposed contained a polymer molecule having a molecular weight distribution and a crosslinking degree distribution, and hence the temperature range of the decomposition involving the release of the monomers became wide. In the peaks derived from the random scission of the main chain and the depolymerization resulting from the random scission, the peak top temperature of the peak at the lower temperature was 396.6° C. and the peak top temperature of the peak at the higher temperature was 419.0° C. The peak observed at 396.6° C. is the peak at which vinylpyridine and ethyl vinyl benzene start to desorb, and the peak observed at 419.0° C. is the peak at which the desorption of vinylpyridine and ethyl vinyl benzene ends.

In addition, in each of the samples 1 to 5, the same peaks as those of the sample 0 were observed. However, the peak (characteristic peak) of the unused sample 0 observed at 396.6° C. shifted to lower temperatures as the decomposition ratio increased. It should be noted that the peak top temperature of the peak (reference peak) of the unused sample 0 observed at 419.0° C. remained nearly unchanged even when the decomposition ratio increased.

Figure 6:
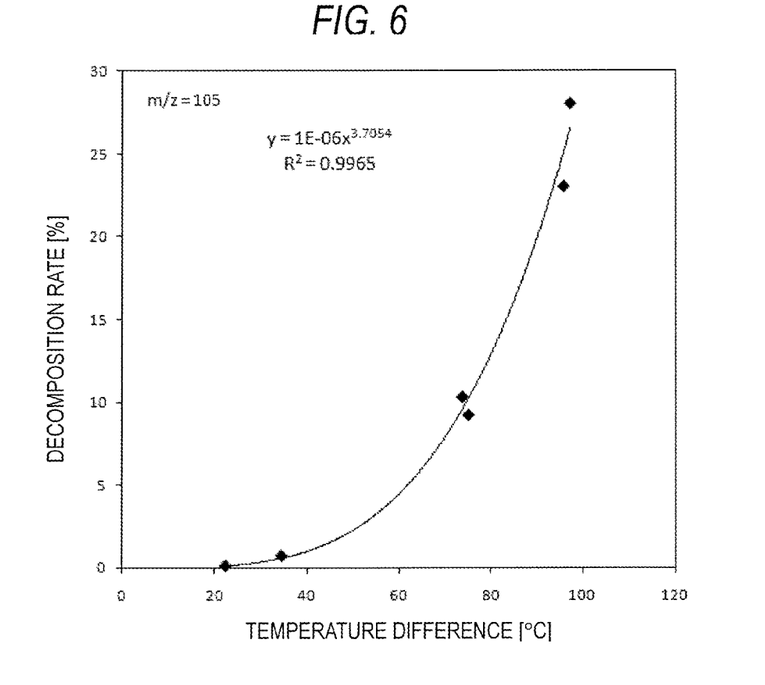
FIG. 6 is a graph showing a relationship between a difference in peak top temperature in the profiles at an m/z of 105 and the decomposition ratio of the resin.
Figure 7:
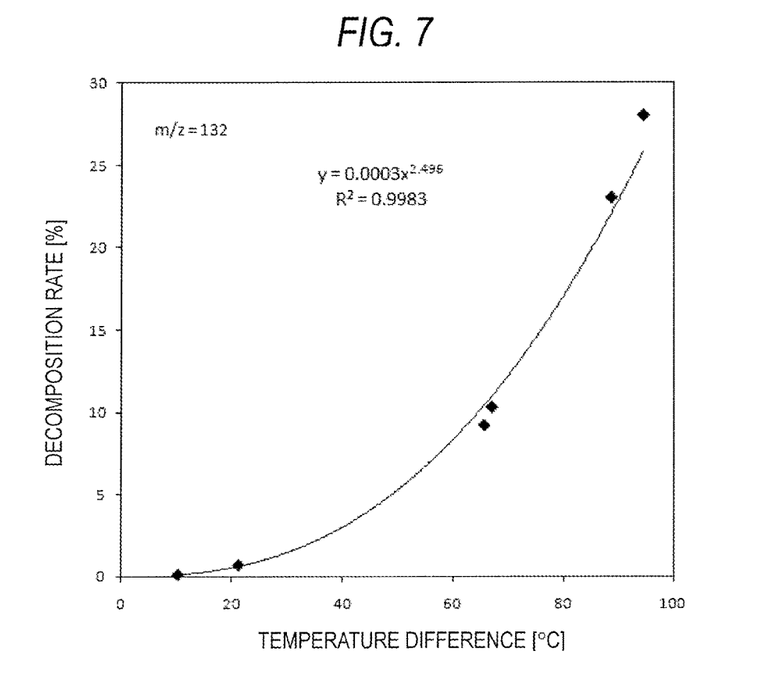
FIG. 7 is a graph showing a relationship between a difference in peak top temperature in the profiles at an m/z of 132 and the decomposition ratio of the resin.

In each of the vinylpyridine (m/z=105) profiles and ethyl vinyl benzene (m/z=132) profiles of the samples 0 to 5 having different decomposition ratios, a temperature difference between the peak (characteristic peak) at which the desorption started and the peak (reference peak) at which the desorption ended was determined and plotted against the decomposition ratio of the resin. FIG. 6 shows a relationship between the difference in peak top temperature between the peaks and the decomposition ratio of the resin in the profiles at an m/z of 105. In addition, FIG. 7 shows a relationship between the difference in peak top temperature between the peaks and the decomposition ratio of the resin in the profiles at an m/z of 132. As can be seen from FIG. 6 and FIG. 7, in each of vinylpyridine (m/z=105) and ethyl vinyl benzene (m/z=132), the temperature difference between the characteristic peak and the reference peak has an extremely high correlation with the decomposition ratio of the resin.

Therefore, the deterioration degree of the resin can be determined as described below. A relationship between the decomposition ratio of the same resin as the resin to be evaluated, and the temperature difference between the characteristic peak and reference peak of the TG-MS analysis is determined in advance, the resin to be evaluated is subjected to the TG-MS analysis by a temperature increase, and the temperature difference between the characteristic peak and the reference peak is determined. That is, the difference in peak top temperature can be an indicator for the evaluation of the deterioration degree of the resin.

<Analysis of DTG Profile>

Figure 8:
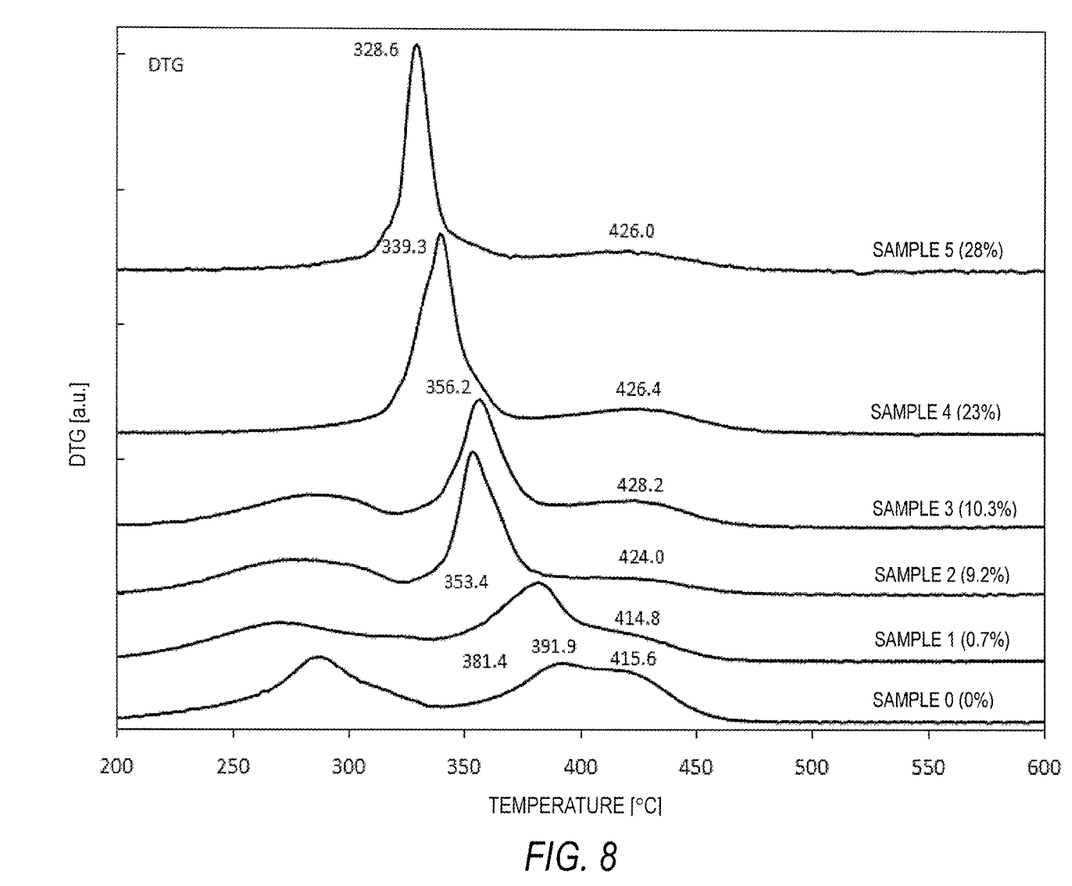
FIG. 8 is a graph showing the DTG profiles of the samples 0 to 5.

FIG. 8 shows DTG profiles obtained in the TG-MS analysis. A temperature indicated by the axis of abscissa of FIG. 8 is the temperature of the resin. As shown in FIG. 8, the following peaks were observed: a peak (reference peak) that was observed at around 414° C. to 428° C. and whose peak top temperature was hardly changed by the decomposition ratio, and a peak (characteristic peak) that was observed at a temperature lower than that of the reference peak and whose peak top shifted to lower temperatures from around 392° C. to 328° C. as the decomposition ratio increased.

Figure 9:
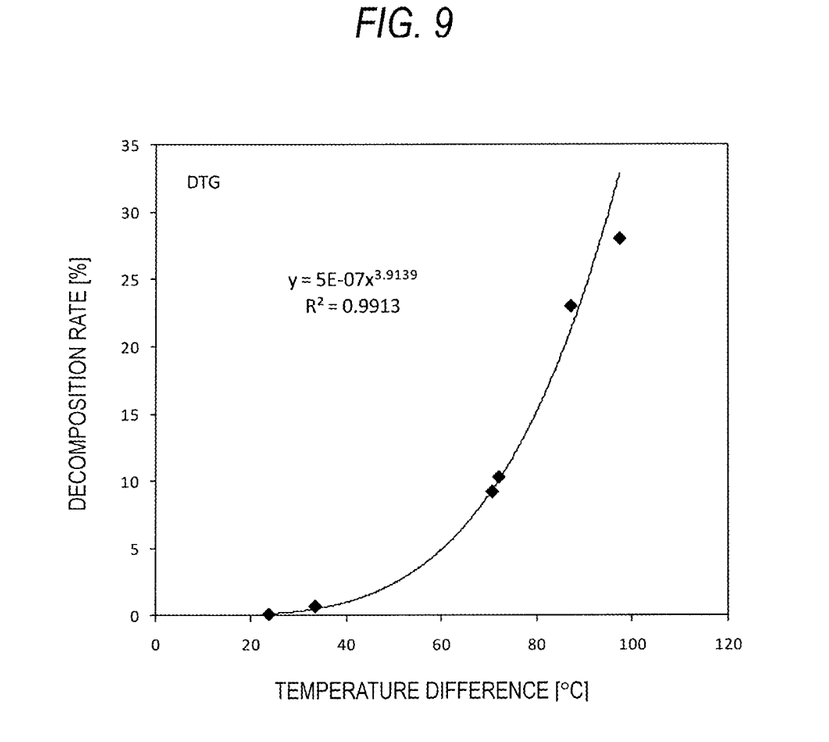
FIG. 9 is a graph showing a relationship between a difference in peak top temperature in the DTG profiles and the decomposition ratio of the resin of the samples 0 to 5.

In each of the DTG profiles of the samples 0 to having different decomposition ratios, a temperature difference between the peak (characteristic peak) at which the desorption started and the peak (reference peak) at which the desorption ended was determined and plotted against the decomposition ratio of the resin. FIG. 9 shows a relationship between the difference in peak top temperature and the decomposition ratio of the resin in the DTG profiles of the samples 0 to 5. As can be seen from FIG. 9, the temperature difference between the characteristic peak and the reference peak has an extremely high correlation with the decomposition ratio of the resin.

As described above, the deterioration degree of a resin can be evaluated with ease and high accuracy by using a characteristic peak that shifts to lower temperatures depending on a decomposition ratio (deterioration degree), the peak being observed in thermal analysis such as TG-MS or DTG. In particular, the deterioration of the resin can be evaluated with higher accuracy by determining a difference in peak top temperature between the peak and a peak (reference peak) whose peak top position is hardly changed by the decomposition of the resin.

The deterioration degree of a resin can be evaluated with high accuracy and ease by using information based on the shift of a characteristic peak representing the deterioration degree of the resin, the peak being observed in thermal analysis by a temperature increase, to lower temperatures. Further, the deterioration degree of the resin can be evaluated with high accuracy and ease by heating the resin to cause depolymerization resulting from random scission of a main chain of the resin, measuring a temperature of the resin at which the depolymerization occurs and evaluating a deterioration degree of the resin based on the measured temperature. The evaluation can be quantitatively performed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-241927, filed Nov. 22, 2013, which is hereby incorporated by reference herein in its entirety.

What is claimed is:

1. A method of evaluating a resin, the method comprising evaluating the resin based on a shift of a characteristic peak representing a deterioration degree of the resin to lower temperatures, wherein the characteristic peak is observed in thermal analysis of the resin in which a sample of the resin is heated over a temperature range and wherein the resin comprises a resin having a side chain having a nitrogen-containing aromatic ring group and a crosslinking portion.

2. A method of evaluating a resin according to claim 1, wherein the evaluating the resin is performed based on a temperature difference between the characteristic peak and another peak except the characteristic peak.

3. A method of evaluating a resin according to claim 1, wherein the resin comprises a catalyst obtained by causing a crosslinked vinylpyridine resin to carry a rhodium complex, the catalyst being used as a catalyst in a method of producing acetic acid based on a methanol carbonylation reaction.

4. A method of evaluating a resin,
the method comprising:
heating the resin in a temperature range to cause depolymerization resulting from random scission of a main chain of the resin;
measuring a temperature of a characteristic peak of the resin at which the depolymerization occurs; and
evaluating a deterioration degree of the resin based on a shift of the measured temperature of the characteristic peak to lower temperatures,
wherein the resin comprises a resin having a side chain having a nitrogen-containing aromatic ring group and a crosslinking portion.

* * * * *